(12) United States Patent
Li et al.

(10) Patent No.: US 10,080,890 B2
(45) Date of Patent: Sep. 25, 2018

(54) IMPLANTABLE BIOLOGICAL ELECTRODE AND MEDICAL ASSEMBLY INCLUDING THE SAME

(75) Inventors: Luming Li, Beijing (CN); Changqing Jiang, Beijing (CN); Hongwei Hao, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 137 days.

(21) Appl. No.: 14/238,567

(22) PCT Filed: Oct. 17, 2011

(86) PCT No.: PCT/CN2011/080859
§ 371 (c)(1),
(2), (4) Date: May 30, 2014

(87) PCT Pub. No.: WO2013/023404
PCT Pub. Date: Feb. 21, 2013

(65) Prior Publication Data
US 2014/0288618 A1   Sep. 25, 2014

(30) Foreign Application Priority Data
Aug. 12, 2011   (CN) .......................... 2011 1 0231234

(51) Int. Cl.
*A61B 5/05*   (2006.01)
*A61B 5/04*   (2006.01)
(Continued)

(52) U.S. Cl.
CPC ................. *A61N 1/08* (2013.01); *A61N 1/05* (2013.01); *B82Y 5/00* (2013.01); *B82Y 30/00* (2013.01); *A61N 1/086* (2017.08)

(58) Field of Classification Search
CPC .. A61N 1/05; A61N 2001/086; A61N 1/0534; A61N 1/0529; A61N 1/0531;
(Continued)

(56) References Cited

U.S. PATENT DOCUMENTS

| 4,437,474 A | 3/1984 | Peers-Trevarton |
| 4,458,695 A | 7/1984 | Peers-Trevarton |

(Continued)

FOREIGN PATENT DOCUMENTS

| CN | 1388540 A | 1/2003 |
| CN | 101109098 A | 1/2008 |

(Continued)

OTHER PUBLICATIONS

Owston "Electrical properties of single carbon fibres". Journal of Physics. vol. 3. 1970.*

*Primary Examiner* — Joseph Stoklosa
*Assistant Examiner* — Brian M Antiskay
(74) *Attorney, Agent, or Firm* — Novick, Kim & Lee, PLLC; Allen Xue (57) ABSTRACT

An implantable biological electrode, including a wire (2), wherein two ends of the wire (2) are connected with a contact (1) and a connector (3) respectively. The contact (1) comprises a conductive non-magnetic nanofiber with a specific resistivity or a conductive film with a specific center resistivity. A medical assembly comprises the implantable biological electrode. A contact prepared by the winding of a nanofiber or film material with a relatively high resistivity can effectively suppress turbulence and improve the safety of the electrode during magnetic resonance imaging.

11 Claims, 6 Drawing Sheets

(51) Int. Cl.
*A61N 1/08* (2006.01)
*A61N 1/05* (2006.01)
*B82Y 30/00* (2011.01)
*B82Y 5/00* (2011.01)

(58) Field of Classification Search
CPC .............. A61N 1/0556; A61B 18/1492; A61B 2018/00839; A61B 2019/5236; A61B 5/04001; A61B 5/042; A61B 5/6852; A61B 2019/5466; A61B 5/6868
USPC ........ 600/372–373, 377–378, 393, 544–545, 600/395; 607/115–118
See application file for complete search history.

(56) References Cited

U.S. PATENT DOCUMENTS

| | | | | |
|---|---|---|---|---|
| 5,331,959 A * | 7/1994 | Imran | .................. | A61B 5/0408 252/500 |
| 5,336,254 A | 8/1994 | Brennen et al. | | |
| 5,411,527 A * | 5/1995 | Alt | ...................... | A61N 1/0587 600/374 |
| 5,702,437 A | 12/1997 | Baudino | | |
| 6,480,747 B2 * | 11/2002 | Schmidt | ............... | A61B 5/0422 607/122 |
| 7,571,010 B2 * | 8/2009 | Zarembo | ................ | A61N 1/056 600/372 |
| 7,844,347 B2 * | 11/2010 | Brabec | ................. | A61N 1/0556 600/372 |
| 8,639,311 B2 * | 1/2014 | Giszter | ................. | G01D 21/00 600/373 |
| 8,855,788 B2 * | 10/2014 | Lloyd | ................. | A61B 5/0422 607/116 |
| 9,414,758 B1 * | 8/2016 | Brockway | ............ | A61B 5/6804 |
| 2005/0203604 A1 * | 9/2005 | Brabec | ................. | A61N 1/056 607/122 |
| 2005/0222659 A1 * | 10/2005 | Olsen | ....................... | A61N 1/05 607/116 |
| 2007/0208383 A1 * | 9/2007 | Williams | ............... | A61N 1/056 607/2 |
| 2008/0183258 A1 * | 7/2008 | Inman | .................. | A61N 1/0558 607/118 |
| 2010/0070007 A1 * | 3/2010 | Parker | ............... | A61M 25/0009 607/116 |
| 2011/0184269 A1 * | 7/2011 | Sauter-Starace | ..... | A61B 5/0478 600/378 |

FOREIGN PATENT DOCUMENTS

| | | |
|---|---|---|
| CN | 101172184 A | 5/2008 |
| CN | 101484628 A | 7/2009 |
| CN | 101927057 A | 12/2010 |
| CN | 102068760 A | 5/2011 |

* cited by examiner

IMPLANTABLE BIOLOGICAL ELECTRODE AND MEDICAL ASSEMBLY INCLUDING THE SAME

CROSS-REFERENCE TO RELATED APPLICATIONS

This application is the U.S. National Phase under 35. U.S.C. § 371 of International Application PCT/CN2011/080859, filed Oct. 17, 2011, which claims priority to Chinese Patent Application No. 201110231234.3, filed Aug. 12, 2011. The disclosures of the above-described applications are hereby incorporated by reference in their entirety. The International Application was published under PCT Article 21(2) in a language other than English.

TECHNICAL FIELD

The present invention relates to the technical field of implantable medical apparatus, and more specifically, to an implantable biological electrode and medical assembly including the same.

BACKGROUND

Magnetic Resonance Imaging (MRI) technology has been more and more widely used in modern medical diagnosis due to its advantages of no radiation, high resolution imaging for soft tissue and developing for brain function. However, nowadays, the risk of radio frequency (RF) heating makes the patients implanted with medical apparatus such as a nerve stimulator or pacemaker, etc. unable to conduct a MRI inspection in high field intensity. The FDA reported a case in which a Parkinson patient implanted with a deep brain stimulator conducted a MRI inspection which caused him in a coma and permanently disabled. This issue makes many patients have a lot of restrictions when they needed to conduct a MRI inspection.

The research shows that, heating mainly occurs at the tip of the metallic implant. For example, for a deep brain stimulator, heating mainly occurs around the contact of the electrode. This is because metal contact will produce turbulence in a RF field of MRI on one hand; and on the other hand, as the electrode acting as an antenna in the RF field, the electric field induced on the electrode will cause heating at the contact.

The heating effect is related to the position and shape of the electrode in a MRI magnetic field. In some specific positions and shapes, the electrode can avoid resonance of a MRI magnetic field so as to avoid over-heating. However, in practical applications, the implanting manner of electrodes in a human body cannot be undetermined, and therefore it is necessary for the electrode itself to meet safety requirement under a resonance condition.

SUMMARY

The technical problem to be solved by the present invention is: how to effectively suppress turbulence for an implantable biological electrode.

In order to solve the technical problem above, the present invention provides an implantable biological electrode comprising a wire, wherein two ends of the wire are connected with a contact and a connector respectively. The contact comprises a conductive non-magnetic nanofiber with a specific resistivity or a conductive film with a specific centre resistivity.

Preferably, the specific centre resistivity is a resistivity which is larger than $10^{-6}$ $\Omega \cdot m$.

Preferably, the non-magnetic nanofiber is selected from carbon nanotube wire, carbon fiber, conductive polymeric fiber, or combinations thereof; and the film is selected from carbon nanotube film, conductive polymeric film, or combinations thereof.

Preferably, the wire is made of conductive non-magnetic material.

Preferably, the wire is selected from platinum, iridium, an alloy of platinum and iridium, carbon nanotube wire, carbon fiber and conductive polymer.

Preferably, the wire is connected with the contact by mechanical connection, welding, or bonding.

Preferably, the biological electrode further comprises a sleeve, with non-magnetic nanofiber or film wound on the sleeve.

Preferably, the wire comprises a leading-out terminal, the non-magnetic nanofiber or film forming the contact is wound at a position of the sleeve where the leading-out terminal of the wire is located so that the contact and the wire can form an electrical connection by means of a mechanical contact.

Preferably, the leading-out terminal has a U-shape, and is overlapped and wound with the non-magnetic nanofiber or film.

Preferably, the non-magnetic nanofiber or film is coated with metallic coating.

The present invention further provides a medical assembly comprises:

the implantable biological electrode; and a signal transceiver, connected to the connector, for generating a specific electrical signal and transmitting the signal to the contact, and/or receiving the electrical signal from the contact and processing the signal.

The technical solution above has the following advantages: a contact of the present invention prepared by the winding of nanofiber or film material with a relatively high resistivity can effectively suppress turbulence, so as to overcome thermal problems under a magnetic resonance environment and improve the safety of the electrode during magnetic resonance imaging.

WITH REFERENCE NUMBERS

1 contact
2 wire
3 connector
4 signal transceiver
5 sleeve
6 leading-out terminal
7 non-magnetic nanofiber or film

SPECIFIC DESCRIPTION OF EMBODIMENTS

The following embodiments are used for illustrating the present invention, but not used for limiting the scope of the present invention.

As shown in FIG. 1 and FIGS. 3-5, an implantable biological electrode of the present invention comprises a wire (2). Two ends of the wire (2) are connected with a contact (1) and a connector (3) respectively, wherein the contact (1) is formed with non-magnetic nanofiber or film (7). The non-magnetic nanofiber or film is wound (preferably wound in multiple layers) on a sleeve (5). The sleeve (5) is used for supporting contact (1) and providing protections for the wire (2) as well as insulation. The wire (2) inside of the sleeve (5) protrudes out at the position of the contact (1) and forms an electrical connection with contact (1). Signals can be transmitted between contact (1) and wire (2). There may be one or several contacts. In this embodiment, there are 4 contacts. The diameter of a non-magnetic nanofiber material or the thickness of a film material can be from a hundred nanometers to several hundreds micrometers.

Figure 1:
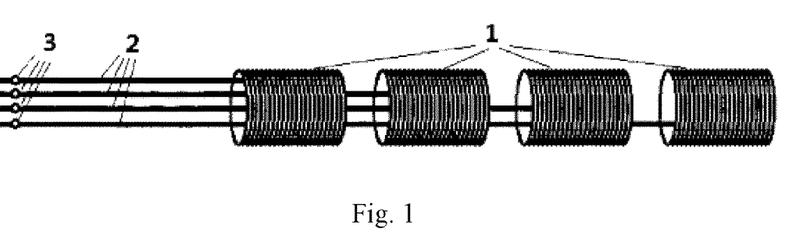
FIG. 1 is a schematic view of an electrode structure according to an embodiment of the present invention.
Figure 2:
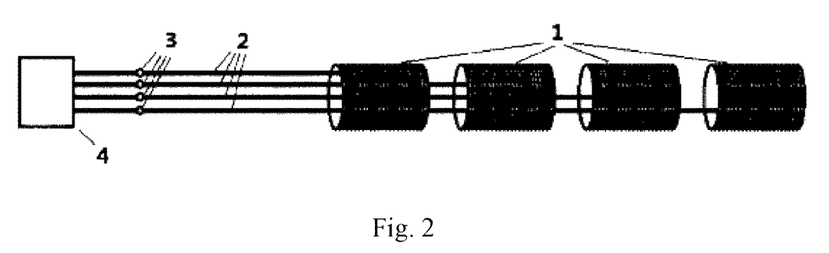
FIG. 2 is a schematic view of the structure of a medical assembly according to an embodiment of the present invention.

As shown in FIG. 2, a medical assembly of the present invention also comprises a signal transceiver (4) in addition to the electrodes above. The signal transceiver (4) is used for generating specific electrical stimulating signals and transmitting them to the contacts of said electrodes and/or receiving biological electrical signals from the contacts of said electrodes and conducting a specific processing for the biological electrical signals.

As the heating issue caused by RF in MRI mainly occurs around the contact of the electrode, this heating issue is resulted from the turbulence caused by RF at the contact of the electrode and the heating of electromotive force induced in the electrode from the time-varying electrical field caused by RF at the contact of the electrode and surrounding tissues. The influence of this kind of effect is evident for metallic contacts, which will get a very high increase in temperature. In case of critical conditions, it will do great harm to patients. The contact of the present invention prepared by the winding of nanofiber or film material with a relatively high resistivity can effectively suppress turbulence. Firstly, a high resistivity may result a small induced current in the same RF field. Secondly, the contact of the electrode is no longer an integrated material; the layered structure between non-magnetic nanofibers or films effectively cuts off the transmission of induced current, so as to reduce the influence to the smallest degree. The contact of the electrode of the prior art often utilizes materials having a resistivity of $10^{-7}$ $\Omega \cdot m$ or smaller (such as Pt—Ir alloy and other metals, etc.). The present invention presents a selection of film materials with a scale of $10^{-6}$ $\Omega \cdot m$ or with a higher centre resistivity, or a selection of non-magnetic nanofiber with a scale of $10^{-6}$ $\Omega \cdot m$ or with a higher resistivity. The higher centre resistivity or resistivity can achieve better suppression effect; but it needs to meet the requirement of conductivity in order to transmit an effective current in electrical stimulation. The selectable contact materials include non-magnetic nanofiber or film. The non-magnetic nanofiber is selected from carbon nanotube wires, carbon fiber, conductive polymeric fiber, or combinations thereof; and the film is selected from carbon nanotube film, conductive polymeric film, and combinations thereof.

Figure 3:
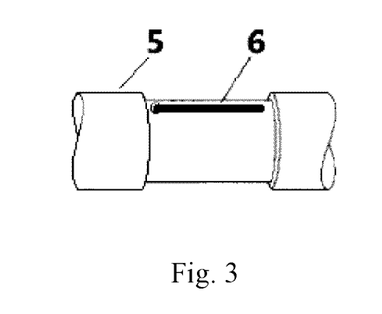
FIGS. 3-5 show the process for making a contact.
Figure 4:
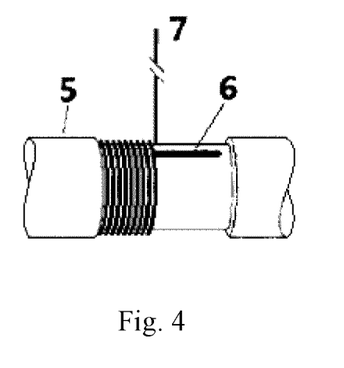
Figure 5:
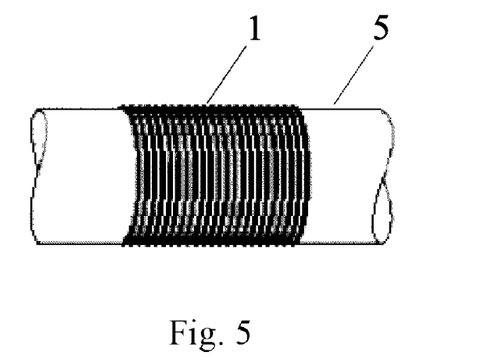

FIGS. 3-5 show the fabrication process of the contact in an embodiment of the present invention. One of the contacts is taken as an example for illustration.

First, a sleeve (5) is provided; and the wire (2) is led out from the sleeve (5) to form a leading-out terminal (6) as is shown in FIG. 3. The sleeve (5) is made of biologically safe macromolecule materials selected from polyurethane, silicon rubber, nylon or combinations thereof. For the convenience of controlling the positions and shapes of the contact, a groove is processed on the outer wall of the sleeve. The groove can be made by mechanical processing or hot molding, etc. The leading-out terminal (6) is attached to the outer wall of the sleeve. The wire (2) is normally made of biologically safe conductive non-magnetic materials selected from platinum, iridium, an alloy of them, carbon nanotube wire, carbon fiber and conductive polymer.

Figure 6:
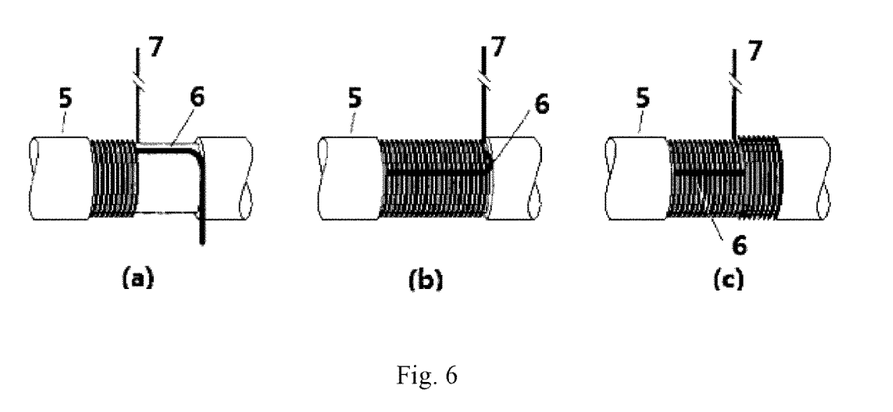
FIG. 6 is a schematic view of one of the connecting patterns of the wire and the contact as well as a fabrication process thereof.

The non-magnetic nanofiber or film (7) is wound at a position of the sleeve (5) where the leading-out terminal (6) of the wire (2) is located to form a mechanical contact with the leading-out terminal (6) of the wire (2) so as to form an electrical connection as is shown in FIG. 4. The winding is continued until the leading-out terminal (6) of the wire (2) is covered; and the winding can be done for one layer or several layers. The shape after processing is shown as FIG. 5. There are many patterns of connections between the wire and the contact. FIG. 6 shows a relatively complicated mechanical connection manner, wherein (a), (b) and (c) show a fabrication process: the leading-out terminal (6) of the wire (2) is folded into a U-shape and is overlapped and wound with the non-magnetic nanofiber or film to improve connectivity between the wire and the contact. The wire and the contact can also be welded together by laser, etc. The sleeve (5) can be partly or entirely coated with a metallic coating by means of electroplating, sputtering and/or deposition to increase connectivity; or the wire and the contact are bonded with a biologically safe conductive glue. The ends wound with the non-magnetic nanofiber or film can be adhered on the wall of the sleeve by means of a biologically compatible adhesive to prevent the contact from loosing and dropping.

The manufacturing manner of the electrode of the present invention is easier than the traditional process. And the electrode of the present invention has a good electrode interface, and can overcome thermal problems under a magnetic resonance environment and improve the safety of the electrode during magnetic resonance imaging. It can be used in nerve electrical stimulations, heart inside electrical stimulations, muscle electrical stimulations, spinal cord electrical stimulations, and other similar applications.

INDUSTRIAL PRACTICAL APPLICABILITY

The present invention provides an implantable biological electrode and a medical assembly including the same, wherein a contact prepared by the winding of nanofiber or film material with a relatively high resistivity can effectively suppress turbulence, so as to overcome thermal problems under a magnetic resonance environment and improve the safety of the electrode during magnetic resonance imaging. The present invention has industrial applicability.

What is claimed is:

1. An implantable biological electrode for deep brain simulation, comprising:
   a wire having a first end and a second end;
   a sleeve that sleeves over a portion of the wire; and
   a contact formed by conductive non-magnetic nanofibers wrapped in a coil about an outer wall of the sleeve,
      wherein the coil has one or more layers of the conductive non-magnetic nanofibers in a radial direction,
      the first end of the wire is in contact with the coil, the second end of the wire is connected to a connector,
      the conductive non-magnetic nanofibers has a specific center resistivity or a specific resistivity, respectively, larger than $10^{-6}$ $\Omega \cdot m$, whereby a heat generation is suppressed at the contact when the contact is exposed to a radio frequency (RF) field, and the conductive non-magnetic nanofibers are selected from the group consisting of carbon nanotube wire, carbon fiber, and combinations thereof.

2. The implantable biological electrode of claim 1, wherein the wire is made of a conductive non-magnetic material.

3. The implantable biological electrode of claim 2, wherein the wire is selected from the group consisting of platinum, iridium, an alloy of platinum and iridium, carbon nanotube wire, carbon fiber, and conductive polymer.

4. The implantable biological electrode of claim 1, wherein the wire is connected with the contact by mechanical connection or welding.

5. The implantable biological electrode of claim 1, wherein the sleeve comprises at least one groove on the outer wall of the sleeve, and the coil is disposed about the at least one groove.

6. The implantable biological electrode of claim 5, wherein the first end of the wire is affixed to the outer wall of the sleeve in the at least one groove, forming an electrical connection to the coil disposed about the at least one groove of the sleeve.

7. The implantable biological electrode of claim 6, wherein the first end of the wire forms a U-shape, and is overlapped and wound with the conductive non-magnetic nanofiber.

8. The implantable biological electrode of claim 5, wherein the conductive non-magnetic nanofibers is coated with a metallic coating.

9. A medical assembly comprising:
the electrode according to claim 1; and
a signal transceiver connected to the connector for generating a specific electrical signal and transmitting the signal to the contact, or receiving the electrical signal from the contact and processing the signal, or both.

10. The implantable biological electrode of claim 1, wherein the sleeve comprises a biologically safe macromolecule material selected from the group consisting of polyurethane, silicon rubber, nylon, or combinations thereof.

11. The implantable biological electrode of claim 1, wherein the wire is selected from the group consisting of platinum, iridium, an alloy of platinum and iridium, carbon nanotube wire, carbon fiber, and conductive polymer.

* * * * *